United States Patent
Schumann

(10) Patent No.: US 7,487,660 B2
(45) Date of Patent: Feb. 10, 2009

(54) METHOD AND SYSTEM FOR MONITORING THE FUNCTIONAL CAPABILITY OF A PARTICLE DETECTOR

(75) Inventor: Bernd Schumann, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 439 days.

(21) Appl. No.: 10/531,168

(22) PCT Filed: Jun. 24, 2003

(86) PCT No.: PCT/DE03/02097

§ 371 (c)(1),
(2), (4) Date: Dec. 7, 2005

(87) PCT Pub. No.: WO2004/036006

PCT Pub. Date: Apr. 29, 2004

(65) Prior Publication Data

US 2006/0107730 A1   May 25, 2006

(30) Foreign Application Priority Data

Oct. 15, 2002 (DE) ................................ 102 47 977

(51) Int. Cl.
*F01N 11/00* (2006.01)
*G01N 15/00* (2006.01)

(52) U.S. Cl. ............................. 73/1.06; 436/10; 702/116
(58) Field of Classification Search ............. 73/1.06, 73/38; 436/10; 702/116
See application file for complete search history.

(56) References Cited

U.S. PATENT DOCUMENTS

| 5,157,340 A | 10/1992 | Walton et al. |
| 5,458,673 A * | 10/1995 | Kojima et al. .................. 95/11 |
| 6,769,246 B2 * | 8/2004 | Strohmaier et al. ........... 60/297 |
| 6,854,265 B2 * | 2/2005 | Saito et al. ..................... 60/295 |
| 6,935,155 B2 * | 8/2005 | Yasui et al. ................... 73/1.06 |
| 6,975,967 B2 * | 12/2005 | Elwood et al. .......... 702/116 X |
| 6,976,382 B2 * | 12/2005 | Kadowaki et al. ............ 73/1.06 |
| 7,028,466 B2 * | 4/2006 | Kondou et al. ................ 60/295 |
| 2008/0046213 A1 * | 2/2008 | Fregene et al. .............. 702/116 |

FOREIGN PATENT DOCUMENTS

| DE | 198 53 841 A1 | 6/1999 | | |
| EP | 0 506 083 A1 | 9/1992 | | |
| JP | 4-301125 | 10/1992 | | |
| JP | 05141223 A * | 6/1993 | .................. 60/320 |
| JP | 08284643 A * | 10/1996 | | |
| JP | 2003027919 A * | 1/2003 | | |

* cited by examiner

*Primary Examiner*—Thomas P Noland
(74) *Attorney, Agent, or Firm*—Ronald E. Greigg

(57) ABSTRACT

A method and a system for monitoring the functional capability of a particle detector connected downstream, in the flow direction, of a particle filter, in which particles occurring upon the regeneration of the particle filter, in particular ions, are detected by the particle detector and the resultant measurement finding are compared with an expected finding. The measurement and evaluation are effected in a control and evaluation unit. The invention enables monitoring of the functional capability of a particle detector that does not interrupt normal operation and thus increases the reliability of the entire system.

19 Claims, 1 Drawing Sheet

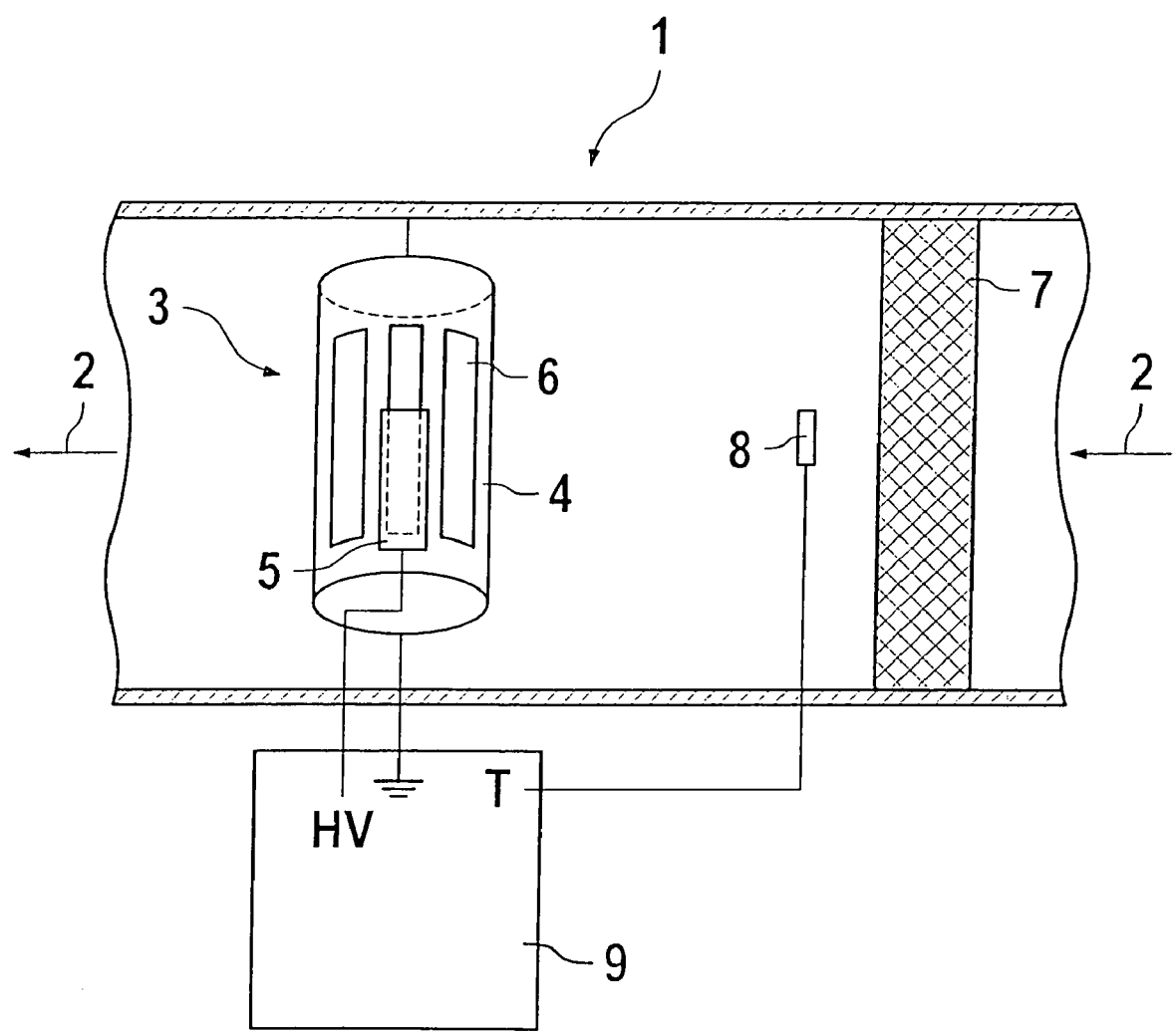

METHOD AND SYSTEM FOR MONITORING THE FUNCTIONAL CAPABILITY OF A PARTICLE DETECTOR

CROSS-REFERENCE TO RELATED APPLICATIONS

This application is a 35 USC 371 application of PCT/DE 03/02097 filed on Jun. 24, 2003.

BACKGROUND OF THE INVENTION

1. Field of the Invention

The invention relates to a method and a system for monitoring the functional capability of a particle detector, using a particle filter connected upstream, in the flow direction, of the particle detector. The invention also relates to a computer program (computer program product) suitable for use in such a system.

2. Prior Art

The concentration of particles, in particular soot particles, in diesel internal combustion engines is often measured by electrical methods. From German Patent Disclosure DE 198 53 584 A1, for instance, a sensor for detecting soot particles is known which includes a first high-voltage electrode and a second ground electrode. In operation, there is a flow of exhaust gas through the space between the electrodes, and either the electrical voltage beyond which sparks occur between the two electrodes, or, if the electrical voltage is kept constant, the magnitude of the ionization current flowing between the two electrodes is used as a standard for the concentration of soot particles in the exhaust gas. Other possibilities are charging the particles by means of an ionization source, such as a corona discharge, or by the combustion process itself. The charged particles are then passed through a suitable detector structure (grid) and can give up their charge again there. The measured current is thus a measure for the charge picked up by the particles, and for a known degree of ionization of the particles, it is also a standard for the number of particles that reach the detector.

Particles that have been charged by one of the methods described above or that become charged on their own from a combustion process can also cause a shift in the charge in a detector structure by influence, which can in turn be proved detected. The known detection methods thus use the measurement of small currents or charge shifts.

For various reasons (to meet legal requirements, and for reasons of safety and environmental aspects), there is a need for the detection devices described above to be monitored for proper functioning. This is true particularly since the charges or charge shifts to be detected are very small, and interference can incorrectly lead to a finding of proper operation.

SUMMARY AND ADVANTAGES OF THE INVENTION

According to the invention, particles that occur in the regeneration of the particle filter are detected by the particle detector, and the resultant measurement finding is compared with an expected finding. In particular, the signal furnished by the particle detector during the measurement can be compared, for instance continuously, with an expected signal.

Particle filters are often regenerated, at certain time intervals or periodically, in order to restore the original filter capacity. For instance, in order to detach soot particles that adhere to the particle filter, soot filters are periodically burned off, from the filter by oxidation processes at high temperatures. According to the invention, a measurement is now performed by the particle detector during this regeneration phase. The particles that occur during the regeneration are detected, and the resultant measurement finding is compared with the finding to be expected. If there are marked deviations in the measurement finding from the expected finding, this is as a rule a clear indication that the particle detector is defective.

By means of the invention, the function of the particle detector can be monitored at periodic intervals, whenever the actual function of the particle detector is not critical, since after all the particle concentration is to be measured only during normal operation. The invention thus assures that during normal operation, the particle detector can function uninterruptedly, and during the filter regeneration, the functional capability of the particle detector can simultaneously be monitored. To that end, the expected finding from the measurement of the particle detector can be determined on the basis of the fill status of the particle filter and on the regeneration conditions. The particle stream that occurs upon regeneration of the particle filter depends primarily on the current fill status (degree of filling) of the filter and on the conditions of the regeneration. From this a model can be developed that makes it possible to determine the expected finding of measurement by the particle detector during the regeneration.

In monitoring the functional capability of soot detectors using a soot filter that is upstream in the flow direction of the soot detector, and that can be regenerated by being burned off, it is advantageous for the ions that occur during the regeneration to be detected by the soot detector. Such soot detectors operate by the measurement methods already described at the outset above.

In this connection, it is advantageous to measure the temperature in, at or downstream of the soot filter, and from the fill status of the soot filter and the measured temperature to determine the expected measurement finding or signal of the soot detector. To that end, a model of the fill status of the soot filter is prepared and correlated for instance with the measured exhaust gas temperature downstream of the soot filter. As the exhaust gas temperature increases, the concentration of ions that are delivered to the detector also increases. This makes it possible to draw a conclusion about the expected finding of measurement by the soot detector, which can then be compared with the finding currently ascertained.

The deviation from the expected finding or measurement finding of the measured signal or measurement finding is preferably compared with a limit value, and if the limit value is exceeded the detector is classified as defective.

It may be advantageous to change the regeneration conditions during monitoring of the functional capability of the particle detector, in order to obtain more-reliable conclusions. For instance, the temperature in burning off the soot filter can be increased, to make it possible to measure a higher, more-conclusive ion concentration. If for instance an exhaust gas temperature of 500° C. is exceeded, then upon regeneration of the soot filter, ions occur in the exhaust gas stream even downstream of the filter, once the filter overall has assumed the higher temperature. These ions are then delivered in a higher concentration to the downstream particle detector. Temperatures between 600° C. and 1000° C. for the burnoff have proved advantageous in this respect.

If a defined temperature range is gone through in the regeneration without an increase in the number of ions, then with high probability a detector flaw is involved.

The invention furthermore proposes a system for monitoring the functional capability of a particle detector, using a particle filter connected upstream of the particle detector in terms of the flow direction, in which a control and evaluation unit is provided, which during the regeneration of the particle filters detects measurement findings furnished by the particle detector and compares them with expected findings.

Moreover, the control and evaluation unit is advantageously designed such that by means of a predetermined model, an expected measurement finding can be determined from the current filter load (filter fill status) and the given regeneration conditions.

Upon the regeneration of a soot filter by burnoff, such a model simply comprises a correlation of the fill status (filter load) of the soot filter and the exhaust gas temperature or filter temperature during the regeneration. The ion current measured at the detector can then be defined as a function of these two variables. Such a model can be ascertained empirically, for instance.

It is advantageous to locate a temperature sensor in, at or downstream, in the flow direction, of the particle filter. If the particle filter is regenerated by heating or burnoff, then such a temperature sensor furnishes an important parameter of the regeneration conditions.

The method described can be implemented by means of a computer program, which can advantageously be placed in the aforementioned control and evaluation unit for execution. The computer program can assure that the various sensors, such as the particle detector or the temperature sensor, will respond at the appropriate time and pick up and or store in memory the appropriate data. The computer program may, from a predetermined model stored in memory, determine expected measurement findings and compare them with the currently measured findings. Deviations can be compared in a simple way with predetermined limit values, from which a conclusion can be drawn about the functional capability of the particle detector. A computer program of this kind can advantageously be executed in the aforementioned control and evaluation unit and can assure periodic monitoring of the functional capability of the particle detector.

The computer program can be stored in memory on suitable data media, such as EEPROMs, flash memories, or CD-ROMs, diskettes, or hard drives. Another option is to download the computer program from an external server, for instance over the Internet.

BRIEF DESCRIPTION OF THE DRAWINGS

The invention is described in further detail herein below, with reference to an exemplary embodiment, in conjunction with the single drawing FIGURE which schematically shows a system for monitoring the functional capability of a particle detector according to the invention.

DESCRIPTION OF THE PREFERRED EMBODIMENT

The present invention will be described taking as an example a soot detector 3 and a soot filter 7, which are located in an exhaust gas line 1 of a diesel engine. The drawing shows the flow direction 2 of the exhaust gas in the exhaust gas line 1, the soot filter 7, and the downstream soot detector 3.

The soot detector 3 has a first electrode 5, which is connected to a high-voltage source HV via a line. The second electrode 4 of the soot detector 13 is embodied cylindrically and is connected to ground. The first electrode 5 and second electrode 4 are located coaxially to one another. The second electrode 4 has axial openings, or recesses 6, through which exhaust gas can flow. With the electrode assembly shown, an ion current can be measured that occurs from the arrival of charged particles at the electrodes 4 and 5. To that end, the ground line and the high-voltage line are carried into a control and evaluation unit 9, in which the further processing of the signals then takes place. It is understood that the supply of high voltage can also be done from outside the control and evaluation unit 9.

A temperature sensor 8 is also located downstream of the soot filter 7 in the flow direction 2, and its signals are likewise delivered to the control and evaluation unit 9, at the input marked T.

The system shown in the drawing is suitable for performing the method of the invention, in which whenever the soot filter 7 is burned off, monitoring of the functional capability with the soot detector 3 can be done. To that end, after the regeneration process is started, the ion current through the soot detector 3 is recorded. The ion current increases over the course of time when charged particles move past the soot detector 3. During this time, a temperature measurement is done by the temperature sensor 8. During the regeneration, the temperature downstream and consequently also at the soot filter 7 increases, and it has been found that at elevated temperatures of between 600 and 1000° C., the ion concentration is especially well suited for monitoring the functional capability of the soot detector 3.

Since the ion concentration increases with an increasing temperature, when the soot detector 3 is monitored an increasing ion current must be associated with this. If an increasing ion current is absent, then it is highly likely that a detector flaw is involved.

At the onset of monitoring of the functional capability, a "testable" bit is set to 1. The monitoring is done along with the regeneration of the soot filter 7. The current received by the soot detector 3 during the regeneration and monitoring phase is detected by the control and evaluation unit 9 and compared with a set-point value. This set-point value can be ascertained empirically; a model that determines the set-point value from the measured temperature and the degree of filling of the soot filter 7 is suitable. If the current measured by the soot detector 3 is below the set-point value by a definable limit, then the soot detector 3 can be recognized as defective.

The onset and course of the measurement as well as the evaluation are preferably done by means of a computer program that is contained in the control and evaluation unit 9.

The invention makes it possible to monitor the functional capability of particle detectors, in particular soot detectors, in a way that does not interrupt normal operation, and it thus increases the reliability of the entire system, and in particular the mode of operation of a diesel engine.

The foregoing relates to a preferred exemplary embodiments of the invention, it being understood that other variants and embodiments thereof are possible within the spirit and scope of the invention, the latter being defined by the appended claims.

The invention claim is:

1. A method for monitoring the functional capability of a particle detector (3) in a gas flow stream, using a regenerated particle filter (7) connected upstream of the particle detector (3) in terms of the flow direction (2), the method comprising,
    regenerating the particle filter,
    detecting particles that occur in the regeneration of the particle filter (7) by the particle detector (3), and
    comparing the resultant measurement finding with an expected finding.

2. The method of claim 1, wherein the expected finding from the measurement of the particle detector (3) is determined on the basis of the fill status of the particle filter (7) and on the regeneration conditions.

3. The method of claim 2, wherein the particle filter comprises a soot filter (7) and wherein the particle detector comprises a soot detector (3), and further comprising
using the soot filter (7) which can be regenerated by being burned off, and detecting ions that occur during the regeneration by the soot detector (3).

4. The method of claim 2, wherein, during the monitoring of the functional capability of the particle detector (3), the regeneration conditions are changed by increasing the temperature in the environment of a soot filter (7) which comprises the particle filter.

5. The method of claim 1, wherein the particle filter comprises a soot filter (7) and wherein the particle detector comprises a soot detector (3), and further comprising
using the soot filter (7) which can be regenerated by being burned off, and detecting ions that occur during the regeneration by the soot detector (3).

6. The method of claim 5, further comprising
measuring the temperature in, at or downstream in the flow direction (2) of the soot filter (7), and
determining the expected finding of the measurement by the soot detector (3) from the fill status of the soot filter (7) and the measured temperature.

7. The method of claim 5, wherein, during the monitoring of the functional capability of the particle detector (3), the regeneration conditions are changed by increasing the temperature in the environment of the soot filter (7).

8. The method of claim 5, wherein for regeneration of the soot filter (7), the temperature in its environment is increased to above 500° C.

9. A computer program with program code means, for performing the steps of claim 8, and executing said computer program on a system for monitoring the functional capability of a particle detector (3), using a regeneratable particle filter (7) connected upstream of the particle detector (3) in terms of flow direction (2), the system comprising,
means for regenerating the filter (7), and
a control and evaluation unit (9), operable during the regeneration of the particle filters (7) to detect measurement findings furnished by the particle detector (3) and compare the detected measurements with expected findings.

10. The method of claim 1, further comprising determining the deviation of the measurement finding from the expected finding and comparing the deviation with a limit value, and if the limit value is exceeded the particle detector (3) is classified as defective.

11. The method of claim 10, wherein, during the monitoring of the functional capability of the particle detector (3), the regeneration conditions are changed by increasing the temperature in the environment of a soot filter (7) which comprises the particle filter.

12. The method of claim 10, wherein for regeneration of the soot filter (7), the temperature in its environment is increased to above 500° C.

13. The method of claim 1, wherein, during the monitoring of the functional capability of the particle detector (3), the regeneration conditions are changed by increasing the temperature in the environment of a soot filter (7) which comprises the particle filter.

14. The method of claim 13, wherein for regeneration of the soot filter (7), the temperature in its environment is increased to above 500° C.

15. A computer program with program code means, for performing the steps of claim 1, and executing said computer program on a system for monitoring the functional capability of a particle detector (3), using a regeneratable particle filter (7) connected upstream of the particle detector (3) in terms of flow direction (2), the system comprising,
means for regenerating the filter (7), and
a control and evaluation unit (9), operable during the regeneration of the particle filters (7) to detect measurement findings furnished by the particle detector (3) and compare the detected measurements with expected findings.

16. A computer program product with program code means which are stored in memory on a computer-readable data medium, for performing the method of claim 1, and executing said computer program on a system for monitoring the functional capability of a particle detector (3), using a regeneratable particle filter (7) connected upstream of the particle detector (3) in terms of flow direction (2), the system comprising,
means for regenerating the filter (7), and
a control and evaluation unit (9), operable during the regeneration of the particle filters (7) to detect measurement findings furnished by the particle detector (3) and compare the detected measurements with expected findings.

17. A system for monitoring the functional capability of a particle detector (3), using a regeneratable particle filter (7) connected upstream of the particle detector (3) in terms of flow direction (2), the system comprising,
means for regenerating the filter (7), and
a control and evaluation unit (9), operable during the regeneration of the particle filters (7) to detect measurement findings furnished by the particle detector (3) and compare the detected measurements with expected findings.

18. The system of claim 17, wherein the control and evaluation unit (9) is designed such that by means of a predetermined model, an expected measurement finding can be determined from the current fill status of the filter and the given regeneration conditions.

19. The system of claim 17, further comprising a temperature sensor (8) located in, at or downstream in the flow direction (2) of the particle filter (7).

* * * * *